(12) United States Patent
Hoctor et al.

(10) Patent No.: US 7,470,232 B2
(45) Date of Patent: Dec. 30, 2008

(54) METHOD AND APPARATUS FOR NON-INVASIVE ULTRASONIC FETAL HEART RATE MONITORING

(75) Inventors: Ralph T. Hoctor, Saratoga Springs, NY (US); Kai E. Thomenius, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 658 days.

(21) Appl. No.: 10/838,799

(22) Filed: May 4, 2004

(65) Prior Publication Data

US 2005/0251044 A1 Nov. 10, 2005

(51) Int. Cl.
*A61B 8/00* (2006.01)

(52) U.S. Cl. .................................................. 600/453

(58) Field of Classification Search ......... 600/453–457, 600/500–503, 511, 528, 588, 591, 437
See application file for complete search history.

(56) References Cited

U.S. PATENT DOCUMENTS

| | | | | |
|---|---|---|---|---|
| 3,552,382 A | * | 1/1971 | Mount | 600/453 |
| 4,489,726 A | * | 12/1984 | Epstein et al. | 600/300 |
| 5,529,073 A | | 6/1996 | Kielbasiewicz | |
| 6,454,716 B1 | * | 9/2002 | Zumeris | 600/453 |
| 7,022,077 B2 | * | 4/2006 | Mourad et al. | 600/449 |

OTHER PUBLICATIONS

"Entwurf Und Erprobung Eines Systems Zur Automatischen Verfolgung Sich Langsam Bewegender Objekte Mit Ultraschall"; Westhues, Dirk; am Institut fur Hochfrequenztechnik Ruhr-Universitat, Bochum; vorgelegt im Sep. 1994. (English translation provided).

* cited by examiner

*Primary Examiner*—Brian L. Casler
*Assistant Examiner*—Jacqueline Cheng
(74) *Attorney, Agent, or Firm*—Fletcher Yoder (57) ABSTRACT

A continuous, non-invasive fetal heart rate measurement is produced using one or more ultrasonic transducer array patches that are adhered or attached to the mother. Each ultrasound transducer array is operated in an autonomous mode by a digital signal processor to obtain data from which fetal heart rate information can be derived. Each ultrasonic transducer array patch comprises a multiplicity of subelements that are switchably reconfigurable to form elements having different shapes, e.g., annular rings. Each subelement comprises a plurality of interconnected cMUT cells that are not switchably disconnectable. The use of cMUT patches will provide the ability to interrogate a three-dimensional space electronically (i.e. without mechanical beam steering) with ultrasound, using a transducer device that is thin and lightweight enough to stick to the patient's skin like an EKG electrode. The ultrasound device can track the fetal heart in three-dimensional space as it moves due to the mother's motion or the motion of the unborn child within the womb.

33 Claims, 4 Drawing Sheets

METHOD AND APPARATUS FOR NON-INVASIVE ULTRASONIC FETAL HEART RATE MONITORING

BACKGROUND OF THE INVENTION

The present invention generally relates to methods and apparatus for determining the heart rate of a subject, and particularly relates to methods and apparatuses for determining the beat-to-beat heart rate of a fetus.

Fetal monitoring (i.e., monitoring of the fetal condition during gestation and at birth) usually comprises monitoring uterine activity and the fetal beat-to-beat heart rate. The fetal heart rate, which provides an indication of whether the fetus is sufficiently supplied with oxygen, is preferably calculated from beat to beat.

To obtain a signal indicative of the fetal heart rate prior to rupture of the membranes, a noninvasive monitoring technique must be used. The most widely adopted measurement technique involves measuring the Doppler shift of an ultrasound signal reflected by the moving fetal heart.

In accordance with a known ultrasonic detection technique, an ultrasound transducer array is placed externally on the pregnant woman's abdomen and oriented such that the transmitted ultrasound waves impinge upon the fetal heart. The reflected ultrasound waves are received either by the same or by a different ultrasound transducer array. The Doppler shift of the reflected ultrasound wave is directly related to the speed of the moving parts of the heart, e.g., the heart valves and the heart walls.

To extract the Doppler component from the received ultrasound signal, typically the latter is demodulated. Further processing depends on the specific application. One technique for acquiring an acoustic indication of the heart beat uses autocorrelation. In accordance with the autocorrelation technique, the Doppler signal or the envelope of the Doppler signal is correlated with itself, thus providing significant peaks in time intervals which correspond to periodic components of the Doppler signal that are caused by the fetal heart beat. Such techniques are necessary because the received ultrasound signals contain noise originating from various physiological sources, such as the maternal aorta, movement of the fetus as a whole, and the like.

In prior art devices, a peak trigger device or an equivalent circuit detects the peaks in the autocorrelation function. The beat-to-beat heart rate, computed as the inverse of the time interval between two successive heart beats, is then available for further processing, display and/or recordation.

In clinical applications, the ultrasound transducer array is placed on the maternal abdomen such that the ultrasound waves will impinge upon the fetal heart. The transmitted ultrasound energy is typically in the form of bursts of high-frequency (e.g., 1 MHz) waves. In prior art devices, these bursts are very long in duration, which severely limits the spatial specificity of the resulting measurement. The final effect of this arrangement is to create a system that is more like a continuous wave ultrasound Doppler than it is like a pulsed wave Doppler device. The ultrasound waves reflected by the fetal heart and other fetal tissue are then received by ultrasound transducer array and fed to a demodulator, which produces a signal that is indicative of the Doppler shift of the received ultrasound signal relative to the transmitted signal. This Doppler shift is caused by the moving parts of the fetal heart, in particular the heart walls and the heart valves. The output of the demodulator is then fed to a bandpass filter that removes unwanted components in the Doppler signal. This filtered signal is then fed to an envelope detector, which generates the envelope of the peaks of the Doppler signal. Later the envelope of the Doppler signal is fed to an autocorrelation circuit that correlates the received signal with itself. The result of the autocorrelation function is that periodic components in the received signal are amplified, while non-periodic or stochastic signals (such as signals caused by movement of the fetus or the mother) are largely suppressed, The output of the autocorrelation function is used to calculate the fetal heart rate. The significant peaks in the amplitude of the autocorrelated signal correspond to fetal heart beats and successive peaks are separated by time intervals that are approximately equal. The fetal heart rate is calculated as the inverse of the time interval between two successive peaks in the autocorrelated signal. Alternatively, the heart rate could be calculated by, e.g., computing it over a longer time interval and averaging the time intervals or averaging the heart rate.

One challenge in clinical applications is ensuring that the ultrasonic transducers are properly positioned relative to the fetal heart. Known instrumentation uses a relatively cumbersome array of single-element ultrasound transducers designed to cover the entire maternal abdomen. Unfortunately, as the result of fetal or maternal motion, the alignment of these transducers is such that the transducers fail to capture some echoes from the fetal heart and there will be a loss of heart rate information. When this occurs, the attending nurse must readjust the positioning of the transducer array. The resulting frustration experienced by hospital staff members because of this inconvenience is apparently to the degree that the instrument is often ignored and the mother and fetus do not receive the benefit of monitoring or the assessment of fetal distress. Additionally, in many instances the mother is instructed not to move, so that the fetal heart rate monitor does not lose the reflected ultrasound signal. This is contrary to good practice, since the mother's motion is important in causing the onset of heavy labor. If the mother were able to move around and still have a working fetal monitor, labor could be shortened in many instances.

There is a need for a method and means for continuously monitoring the fetal heart rate without any operator intervention. The method and apparatus should be designed so that the mother is allowed free motion while being monitored. It is also desirable that a more reliable heart rate measurement be provided as compared to current systems.

BRIEF DESCRIPTION OF THE INVENTION

The present invention overcomes the aforementioned drawbacks by using ultrasound to provide input data for the fetal heart rate calculation. In a disclosed embodiment, a continuous, non-invasive fetal heart rate measurement is produced using one or more ultrasonic transducer array patches that are adhered or attached to the mother. Each ultrasound transducer array is operated in an autonomous mode by a digital signal processor to obtain data from which fetal heart rate information can be derived.

In accordance with the disclosed embodiment, each ultrasonic transducer array patch comprises a multiplicity of sub-elements that are switchably reconfigurable to form elements having different shapes, e.g., annular rings. Each subelement comprises a plurality of interconnected capacitive micromachined ultrasonic transducer (cMUT) cells that are not switchably disconnectable. The use of cMUT patches will provide the ability to interrogate a three-dimensional space electronically (i.e. without mechanical beam steering) with ultrasound, using a transducer device that is thin and lightweight enough to stick to the patient's skin like an EKG electrode.

Thus the present invention applies cMUT technology to the monitoring of fetal heart rate in a labor and delivery or ICU setting. The ultrasound device can track the fetal heart in three-dimensional space as it moves due to the mother's motion or the motion of the unborn child within the womb. This will allow the use of a narrower beam and a smaller sample volume than is used by prior art devices, so that less interference will be present in the Doppler signal that is processed to derive the fetal heart rate. While this tracking is taking place, the fetal heart rate can be derived by standard means from the Doppler shift of the ultrasound reflected from the fetal heart.

One aspect of the invention is a method for monitoring fetal heart rate, comprising the following steps: (a) attaching an ultrasonic transducer array comprising micromachined ultrasonic transducers to an area on the exterior of an abdomen of a pregnant woman; (b) controlling the ultrasonic transducer array to transmit beams of pulsed ultrasonic wave energy into the abdomen that are steered at an angle that causes the beams to intersect a fetal heart inside the abdomen; (c) acquiring acoustic data by transducing ultrasound wave energy returned from the abdomen of the pregnant woman after each transmission in step (b), the acoustic data being acquired using relatively short range gates; and (d) calculating a fetal heart rate based at least in part on the acoustic data acquired in step (c).

Another aspect of the invention is a method for monitoring fetal heart rate, comprising the following steps: (a) attaching an ultrasonic transducer array to an area on the exterior of an abdomen of a pregnant woman; (b) controlling the ultrasonic transducer array to scan the abdomen of the pregnant woman by transmitting beams of pulsed ultrasonic wave energy into the abdomen, the beams being steered at different angles; (c) acquiring acoustic data by transducing ultrasound wave energy returned from the abdomen of the pregnant woman after each transmission in step (b), the acoustic data being acquired using long range gates; (d) detecting a pattern in the acoustic data acquired in step (c), the pattern representing a fetal heart signature; (e) controlling the ultrasonic transducer array to transmit beams of pulsed ultrasonic wave energy into the abdomen that have a short range gate, relative to the range gate size in step (c), and are steered at an angle equal to or approximately equal to the angle of a beam transmitted in step (b) that resulted in the detection of the pattern in the acquired data; (f) acquiring acoustic data by transducing ultrasound wave energy returned from the abdomen of the pregnant woman after each transmission in step (e); and (g) calculating a fetal heart rate based at least in part on the acoustic data acquired in step (f).

A further aspect of the invention is a method of tracking a moving fetal heart inside an abdomen of a patient, comprising the following steps: (a) attaching an ultrasonic transducer array comprising micromachined ultrasonic transducers to an area on the exterior of an abdomen of a pregnant woman; (b) scanning a volume inside the abdomen with beams of pulsed ultrasonic wave energy; (c) acquiring acoustic data by transducing ultrasound wave energy returned from the abdomen after each transmission in step (b), the acoustic data being acquired using range gates centered in different sample volumes; (d) determining the signal-to-noise ratio of the acquired acoustic data for each different range gate; and (e) determining which one of the different range gates had the acoustic data which produced a maximum signal-to-noise ratio.

Yet another aspect of the invention is a system for autonomous monitoring of heart rate in a fetus, comprising an array of ultrasonic transducer elements, the array comprising a multiplicity of micromachined ultrasonic transducer cells built on or formed in a substrate, data processing means, and means for delivering signals derived from the output of the array to the data processing means, wherein the data processing means are programmed to perform the following steps: (a) controlling the array to transmit beams of pulsed ultrasonic wave energy; (b) beamforming acoustic data output from the array in response to impinging ultrasound wave energy transmitted to and returned from the fetal heart; and (c) computing the fetal heart rate based on the beamformed acoustic data.

A further aspect of the invention is a system for autonomous monitoring of heart rate in a fetus, comprising an array of ultrasonic transducer elements, data processing means, and means for delivering signals derived from the output of the array to the data processing means, wherein the data processing means are programmed to perform the following steps: (a) controlling the ultrasonic transducer array to scan the abdomen of the pregnant woman by transmitting beams of pulsed ultrasonic wave energy into the abdomen, the beams being steered at different angles; (b) acquiring acoustic data by transducing ultrasound wave energy returned from the abdomen of the pregnant woman after each transmission in step (a), the acoustic data being acquired using long range gates; (c) detecting a pattern in the acoustic data acquired in step (b), the pattern representing a fetal heart signature; (d) controlling the ultrasonic transducer array to transmit beams of pulsed ultrasonic wave energy into the abdomen that are steered at an angle equal to or approximately equal to the angle of a beam transmitted in step (a) that resulted in the detection of the pattern in the acquired data; (e) acquiring acoustic data by transducing ultrasound wave energy returned from the abdomen of the pregnant woman after each transmission in step (d), the acoustic data being acquired using short range gates, relative to those used in step (b); and (f) calculating a fetal heart rate based at least in part on the acoustic data acquired in step (e).

Yet another aspect of the invention is a system for tracking a fetal heart, comprising an array of ultrasonic transducer elements, data processing means, and means for delivering signals derived from the output of the array to the data processing means, wherein the data processing means are programmed to perform the following steps: (a) scanning a volume inside the abdomen with beams of pulsed ultrasonic wave energy; (b) acquiring acoustic data by transducing ultrasound wave energy returned from the abdomen after each transmission in step (a), the acoustic data being acquired using range gates centered in different sample volumes; (c) determining the signal-to-noise ratio of the acquired acoustic data for each different range gate; and (d) determining which one of the different range gates had the acoustic data which produced a maximum signal-to-noise ratio.

Other aspects of the invention are disclosed and claimed below.

BRIEF DESCRIPTION OF THE DRAWINGS

Reference will now be made to the drawings in which similar elements in different drawings bear the same reference numerals.

DETAILED DESCRIPTION OF THE INVENTION

In accordance with one embodiment of the present invention, one or more cMUT patches are adhered to the mother's abdomen. Each such patch is acoustically coupled to the mother's skin, either by the use of an adhesive with the appropriate speed of sound or by use of an exterior adhesive rim that holds the patch to the mother's skin and encloses an acoustical coupling agent in contact with both the active probe elements and the mother's skin. Each cMUT patch comprises a two-dimensional ultrasound transducer array the focal point of whose beam is steerable in three-dimensional space. The cMUT patches are electrically connected to a bedside instrument.

When the instrument is powered on, a search is performed to acquire the Doppler signal of the fetal heart. An initial coarse search, using wide beams and long range gates, will be followed by higher-resolution searches that will successively locate the fetal heart to a greater precision. Once the fetal heart has been located precisely, its position will be tracked using multiple sample volumes surrounding the heart's location. The sample volume that is directly over the heart's location will produce a Doppler waveform that can be processed to extract the fetal heart rate.

Based on acoustic data from the cMUT patch probes, a processor incorporated in the bedside instrument autonomously computes various parameters, including the estimated fetal heart rate. In addition, the processor forms and steers ultrasound beams over the volume of space in front of each cMUT patch probe. The cMUT patch probes can be electrically coupled to the processor (or processors) by means of cables. Alternatively, a wireless electrical coupling could be provided.

The foregoing concepts can be easily extended to monitor multiple-birth patients using multiple cMUT patches. Even for a single birth, the use of multiple cMUT patches will produce redundant fetal heart signatures, allowing for enhanced reliability. Note that multiple cMUT patches can be employed in a multiple-birth situation in a mode where each cMUT patch is tracking multiple fetal hearts. This is possible because electronic beam steering allows the ultrasound "look directions" to be changed without any time latency.

Figure 1:
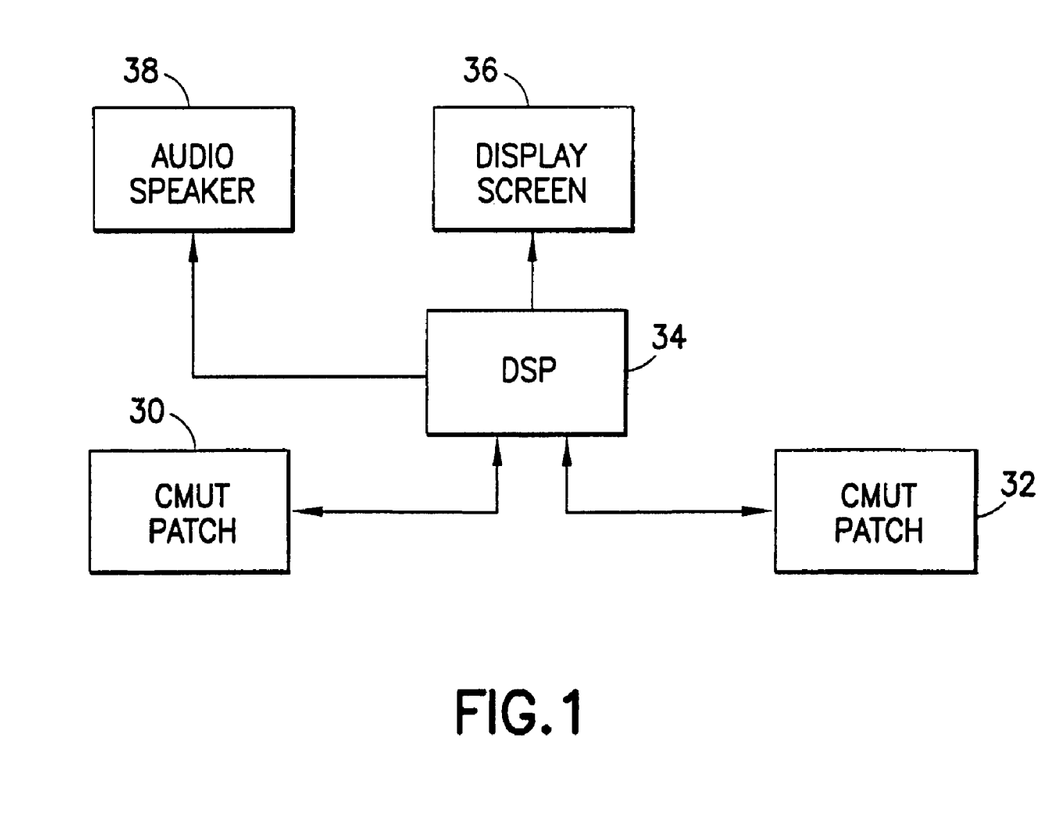
FIG. 1 is a block diagram of a fetal heart rate measurement system in accordance with one embodiment of the invention.

In accordance with one embodiment of the invention shown in FIG. 1, the DSP 34 controls two cMUT patch probes 30 and 32. The reason for having two probes is to have some redundancy in measuring the fetal heart signal. If the mother moves, it is hoped that one or the other probe will remain locked onto the fetal heart. More than two cMUT patch probes can be used. However, it should be understood that the broad concept of the invention also encompasses the use of a single cMUT patch probe.

Referring to the embodiment shown in FIG. 1, the cMUT patch probes 30 and 32 will each operate in a pulsed-wave (PW) Doppler mode. When acquiring the fetal heart, the range gates will be long; this is the standard mode of operation of known ultrasound fetal heart rate monitors. However, the use of cMUT patch probes in conjunction with an instrument operating in the PW Doppler mode provides a beam steering capability that is absent from known fetal heart rate monitoring systems. The fetal heart signature will be obtained by scanning the beams laterally until the fetal heart is detected. This detection occurs because the valves of the fetal heart cause a Doppler shift in the reflected ultrasound. The fetal heart rate is much higher than the maternal heart rate, which makes it easy to recognize. In accordance with one embodiment of the invention, the DSP 34 is programmed to perform an automatic recognition algorithm for the fetal heart signature. For example, the DSP can be programmed to detect an oscillating mean frequency of the Doppler shift in a certain frequency range.

Lateral scanning could be accomplished by translating the transmit aperture or by changing the beam direction from a stationary transmit aperture or a combination of both. However, the use of translation but not beam steering would require the cMUT patch be large enough for a translated aperture to cover a sufficient range of positions.

Once both cMUT patch probes 30 and 32 have acquired the fetal heart, the DSP 34 will begin to decrease the length of the PW range gates. The basic mode of operation will be to decrease the length on one probe until that probe starts to lose signal. A smaller range gate encompassing the heart will give a better signal-to-noise ratio (SNR).

It is possible to use the beam steering angles from the multiple patch probes to guide the process of decreasing the range gate length. For example, if two cMUT patch probes are properly positioned on the mother's abdomen so that two ultrasound beams originate from two points, with the beams at an angle relative to each another and with both beams producing a respective fetal heart signal, then the fetal heart will be located within the spatial intersection of the beams. (The two probes do not have to be transmitting simultaneously in order for this to happen.) If the DSP (or other processor) knew their respective beam steering angles and their relative positions, then the distance of the fetal heart from either probe could be computed, at least approximately, from the geometry of the data collection set-up. The estimated range to the fetal heart could then be used to define a shorter range gate centered around the newly estimated range. However, using the beam steering angles from multiple patch probes to guide the process of decreasing the range gate length is not necessary to practice of the broad concept of the present invention.

The process of adjusting the range gate to optimize the SNR will be in continuous operation as a method of tracking fetal heart range. The method would be a search algorithm based on the Doppler signal power. The range gate would be modified in both size and depth, and changes that resulted in a higher Doppler signal power would be retained. The instrument can identify Doppler signal power because it is the power of that part of the input signal that gets past the high-pass filter used for stationary clutter rejection.

Lateral tracking will occur on one probe at a time. The beam will be steered away from the initial beam steering angle in eight directions, i.e., the eight range gates will surround the range gate of the initial beam in a 3×3 spatial relationship. That direction and range giving the best signal (i.e., highest SNR) will be the new beam steering angle and range gate depth. Extrapolating this principle, one could steer 27 successive beams to acquire data from a cube of range gate positions surrounding the nominal range rate position in three-dimensional space. The implementation of this scheme would require formation of three range gates for each of nine (eight plus the nominal) beam steering angles.

More specifically, the cMUT patch probes can be used to track the location of a fetal heart using a method comprising the following steps: (a) scanning a volume inside the abdomen with beams of pulsed ultrasonic wave energy; (b) acquiring acoustic data by transducing ultrasound wave energy returned from the abdomen after each transmission in step (a), the acoustic data being acquired using range gates centered in different sample volumes; (c) determining the signal-to-noise ratio of the acquired acoustic data for each different range gate; and (d) determining which one of the different range gates had the acoustic data which produced a maximum signal-to-noise ratio. This determined range gate will then be used to acquire additional acoustic data from which the fetal heart rate will be calculated.

Typical frequencies for existing fetal heart rate monitoring probes lie in the range of 1 to 2 MHz. In accordance with one embodiment of the present invention, higher frequencies in the range of about 3 to 5 MHz could be used.

In some known monitors, a speaker is provided and the probe is manually manipulated until the operator hears the fetal heart. The cMUT patch probes disclosed herein can used in conjunction with an instrument operating in such an audio mode. This feature can be utilized to locate the patch probes more accurately at the time of their attachment to the patient's abdomen. For example, the processor may be programmed with a mode whereby the cMUT patch probe is controlled to transmit a series of beams of ultrasonic wave energy in a direction normal to the face of the probe. Acoustic data is acquired by transducing the ultrasound wave energy returned from the abdomen of the patient after each beam transmission. The acquired acoustic data is then converted into audible signals using a speaker 38 (see FIG. 1) connected to the processor 34. The clinician or attending nurse can then attach each cMUT patch probe to the abdomen of the patient at a respective location where the respective audible signals produced using each probe sound like or mimic the fetal heart beat.

In accordance with a further embodiment of the invention, multiple cMUT patch probes can be used to monitor more than one fetus, e.g., twins, inside a patient. The system will monitor twins by assigning a subset of the probes to one fetus and the rest of the probes to the other fetus. If only two cMUT patch probes are used, then each probe will be placed as nearly as possible in positions overlying the respective fetal hearts. When two probes have acquired the same fetal heart, their Doppler mean-frequency traces will be in phase. In general, a second fetal heart will result in a mean-frequency trace that is out of phase.

The disclosed embodiment will operate on complex baseband signals, and will thus be able to track the fetal heart valve motion through a complete cardiac cycle. For example, the DSP will be programmed to compute the mean Doppler frequency on a continuous (every pulse) basis, as is done in color M-mode and using the same computations as those used by a color flow mapper (imaging system). This will produce a simple signed function of time representing the motion that is being sensed within the range gate. This function of time will oscillate at a frequency that is characteristic of the fetal heart.

As seen in FIG. 1, the instrument further comprises a display screen 36 for displaying the fetal heart rate and an image of a PW Doppler flow signal taken from the fetus. The spectrogram is similar to that acquired from an adult heart, except that the signal will evidence a higher heart rate. The PW Doppler spectrogram shows frequency versus time, in which the mean frequency and bandwidth of the signal vary in a periodic manner. The DSP 34 is programmed to locate the fetal heart signal in space by steering the successively transmitted beams until a Doppler signal is acquired that is sufficiently close to being a match of the "signature" signal. There is some ambiguity because the shape of the spectral Doppler output will change with the angle at which the beam intersects the heart, but the rate will always be higher than that of the mother and accordingly it is believed that an automated search would be feasible.

Because the cMUT patches will be adhered to the mother's body, and because the fetal heart is tracked in three-dimensional space as it moves relative to the cMUT patches, the fetal heart rate should be continuously available without any operator intervention. This arrangement has the following advantages. First, operator intervention is eliminated for operation of the fetal heart rate monitor. Second, the mother is allowed free motion while being monitored. Third, the heart rate measurement should be more reliable because the relatively smaller (as compared to current systems) Doppler sample volume will allow a higher Doppler signal-to-noise ratio in the measured ultrasound data. Although similar capabilities will also be available with standard (non-cMUT) two-dimensional arrays and real-time three-dimensional imaging, the cost of these devices is likely to be so high as to rule them out for this application. Additionally, such transducers are too bulky and heavy to be made to adhere to the skin. Furthermore, the use of cMUTs permits a relatively easy and low-cost implementation of concepts such as the mosaic annular array.

The use of ultrasound measurements in the continuous fetal heart rate monitoring application is enabled by micromachined ultrasonic transducer patch probe technology, which allows ultrasound data to be taken using a thin, lightweight probe that adheres to the patient's skin. Recently semiconductor processes have been used to manufacture ultrasonic transducers of a type known as micromachined ultrasonic transducers (MUTs), which may be of the capacitive (cMUT) or piezoelectric (pMUT) variety. cMUTs are tiny diaphragm-like devices with electrodes that convert the sound vibration of a received ultrasound signal into a modulated capacitance. For transmission the capacitive charge is modulated to vibrate the diaphragm of the device and thereby transmit a sound wave.

One advantage of MUTs is that they can be made using semiconductor fabrication processes, such as microfabrication processes grouped under the heading "micromachining". As explained in U.S. Pat. No. 6,359,367:

Micromachining is the formation of microscopic structures using a combination or set of (A) Patterning tools (generally lithography such as projection-aligners or wafer-steppers), and (B) Deposition tools such as PVD (physical vapor deposition), CVD (chemical vapor deposition), LPCVD (low-pressure chemical vapor deposition), PECVD (plasma chemical vapor deposition), and (C) Etching tools such as wet-chemical etching, plasma-etching, ion-milling, sputter-etching or laser-etching. Micromachining is typically performed on substrates or wafers made of silicon, glass, sapphire or ceramic. Such substrates or wafers are generally very flat and smooth and have lateral dimensions in inches.

They are usually processed as groups in cassettes as they travel from process tool to process tool. Each substrate can advantageously (but not necessarily) incorporate numerous copies of the product. There are two generic types of micromachining . . . 1) Bulk micromachining wherein the wafer or substrate has large portions of its thickness sculptured, and 2) Surface micromachining wherein the sculpturing is generally limited to the surface, and particularly to thin deposited films on the surface. The micromachining definition used herein includes the use of conventional or known micromachinable materials including silicon, sapphire, glass materials of all types, polymers (such as polyimide), polysilicon, silicon nitride, silicon oxynitride, thin film metals such as aluminum alloys, copper alloys and tungsten, spin-on-glasses (SOGs), implantable or diffused dopants and grown films such as silicon oxides and nitrides.

The same definition of micromachining is adopted herein. The systems resulting from such micromachining processes are typically referred to as "micromachined electro-mechanical systems" (MEMS).

The use of a MUT patch allows the obstetrician to stick the transducer to the mother's skin. The MUT patch is lightweight and flat. In accordance with one embodiment of the invention, the cMUT patch probes can be attached to the patient's skin with an acoustically transparent layer of adhesive. For the purpose of illustration, a transducer patch will be described that is made up of capacitive micromachined ultrasonic transducers (cMUTs). However, it should be understood that the patch could instead employ pMUTs. The concept of the invention can be extended to cover piezoceramics as well as piezoelectric materials. An embodiment will now be described that incorporates a MUT patch. However, it should be understood that the present invention encompasses not only a device, but also methods for continuous non-invasive fetal heart rate monitoring.

Figures 2, 3:
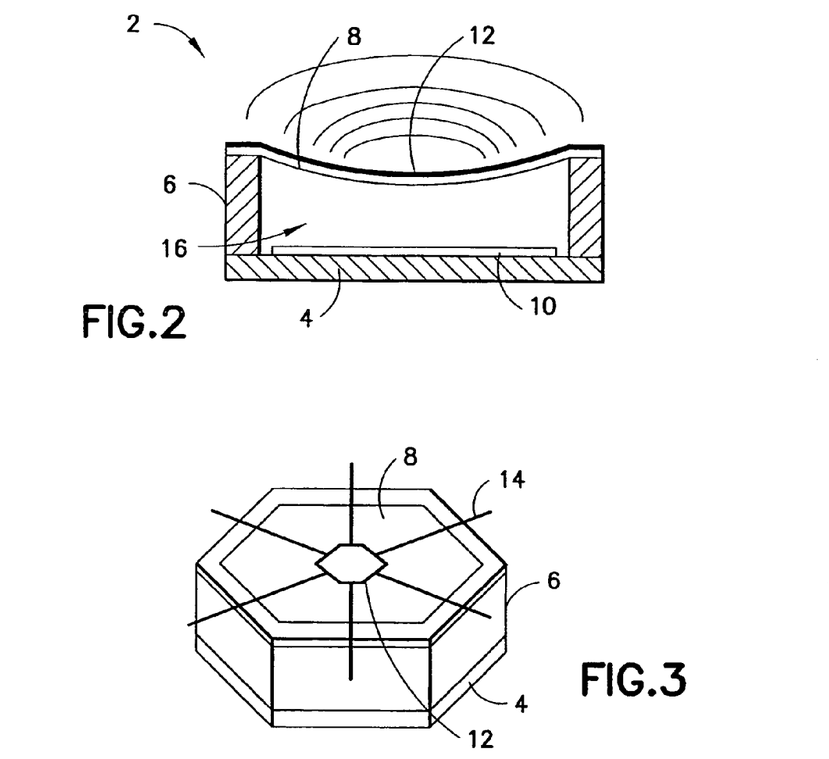
FIG. 2 is a drawing showing a cross-sectional view of a typical cMUT cell.
FIG. 3 is a drawing showing an isometric view of the cMUT cell shown in FIG. 2.

Referring to FIG. 2, a typical cMUT transducer cell 2 is shown in cross section. An array of such cMUT transducer cells is typically fabricated on a substrate 4, such as a heavily doped silicon (hence, semiconductive) wafer. For each cMUT transducer cell, a thin membrane or diaphragm 8, which may be made of silicon nitride, is suspended above the substrate 4. The membrane 8 is supported on its periphery by an insulating support 6, which may be made of silicon oxide or silicon nitride. The cavity 16 between the membrane 8 and the substrate 4 may be air- or gas-filled or wholly or partially evacuated. Typically, cMUTs are evacuated as completely as the processes allow. A film or layer of conductive material, such as aluminum alloy or other suitable conductive material, forms an electrode 12 on the membrane 8, and another film or layer made of conductive material forms an electrode 10 on the substrate 4. Alternatively, the bottom electrode can be formed by appropriate doping of the semiconductive substrate 4.

The two electrodes 10 and 12, separated by the cavity 16, form a capacitance. When an impinging acoustic signal causes the membrane 8 to vibrate, the variation in the capacitance can be detected using associated electronics (not shown in FIG. 2), thereby transducing the acoustic signal into an electrical signal. Conversely, an AC signal applied to one of the electrodes will modulate the charge on the electrode, which in turn causes a modulation in the capacitive force between the electrodes, the latter causing the diaphragm to move and thereby transmit an acoustic signal.

The individual cells can have round, rectangular, hexagonal, or other peripheral shapes. A cMUT cell having a hexagonal shape is shown in FIG. 3. Hexagonal shapes provide dense packing of the cMUT cells of a transducer subelement. The cMUT cells can have different dimensions so that the transducer subelement will have composite characteristics of the different cell sizes, giving the transducer a broadband characteristic.

Unfortunately, it is difficult to produce electronics that would allow individual control over such small cells. While in terms of the acoustical performance of the array as whole, the small cell size is excellent and leads to great flexibility, control is limited to larger structures. Grouping together multiple cells and connecting them electrically allows one to create a larger subelement, which can have the individual control while maintaining the desired acoustical response. So a subelement is a group of electrically connected cells that cannot be reconfigured. For the purpose of this disclosure, the subelement is the smallest independently controlled acoustical unit. One can form rings or elements by connecting subelements together using a switching network. The elements can be reconfigured by changing the state of the switching network. However, individual subelements cannot be reconfigured to form different subelements.

Figure 4:
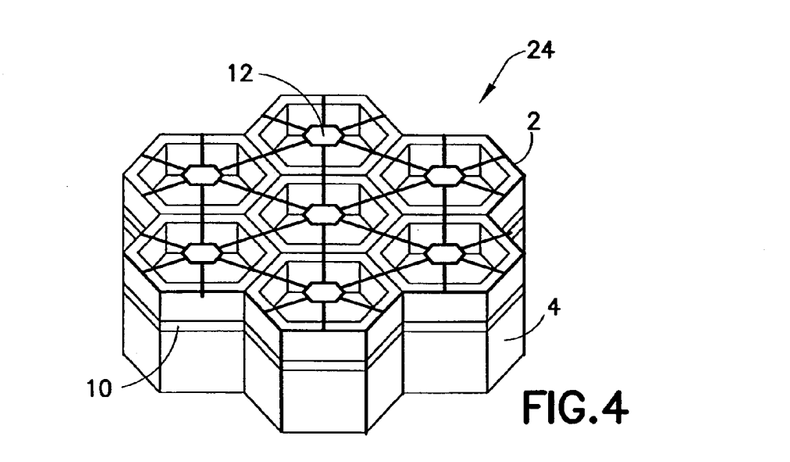
FIG. 4 is a drawing showing an isometric view of a "daisy" subelement formed from seven hexagonal cMUT cells having their top and bottom electrodes respectively electrically interconnected in a manner that is not switchably disconnectable.

For the purpose of illustration, FIG. 4 shows a "daisy" transducer subelement 24 made up of seven hexagonal cMUT cells 2: a central cell surrounded by a ring of six cells, each cell in the ring being contiguous with a respective side of the central cell and the adjoining cells in the ring. The top electrodes 12 of each cell 2 are electrically coupled together by connections that are not switchably disconnectable. In the case of a hexagonal array, six conductors 14 (shown in both FIGS. 3 and 4) radiate outward from the top electrode 12 and are respectively connected to the top electrodes of the neighboring cMUT cells (except in the case of cells on the periphery, which connect to three, not six, other cells). Similarly, the bottom electrodes 10 of each cell 2 are electrically coupled together by connections that are not switchably disconnectable, forming a seven-times-larger capacitive transducer subelement 24.

Figure 5:
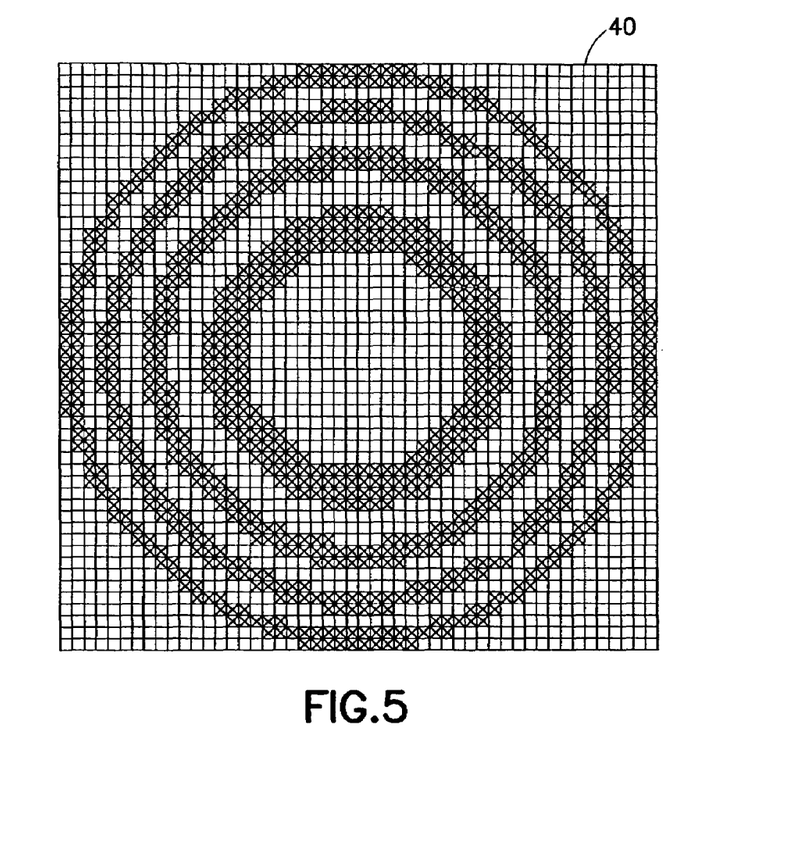
FIG. 5 is a drawing showing a mosaic array comprising eight annular elements.

Subelements of the type seen in FIG. 4 can be arranged to form a two-dimensional array on a semiconductive (e.g., silicon) substrate. These sub-elements can be reconfigured to form elements, such as annular rings, using a switching network. FIG. 5 is a drawing showing a mosaic array 40 comprising eight annular elements. The drawing has been simplified by representing each subelement as a square, the squares being aligned in mutually orthogonal rows and columns. However, it should be understood that the subelements could be of the type shown in FIG. 4, in which case the subelements would be aligned along three axes separated by 60-degree angles.

Reconfigurability using silicon-based ultrasound transducer sub-elements was described in U.S. Pat. No. 6,865,140. One form of reconfigurability is the mosaic annular array, also described in that patent application. The mosaic annular array concept involves building annular elements by grouping subelements together using a reconfigurable electronic switching network. The goal is to reduce the number of beamforming channels, while maintaining image quality and improving slice thickness. To reduce system channels, the mosaic annular array makes use of the fact that for an unsteered beam, the delay contours on the surface of the underlying two-dimensional transducer array are circular. In other words, the iso-delay curves are annuli about the center of the beam. The circular symmetry of the delays leads to the obvious grouping of those subelements with common delays and thus the annular array is born. The reconfigurability can be used to step the beam along the larger underlying two-dimensional transducer array in order to form a scan or image.

Figure 6:
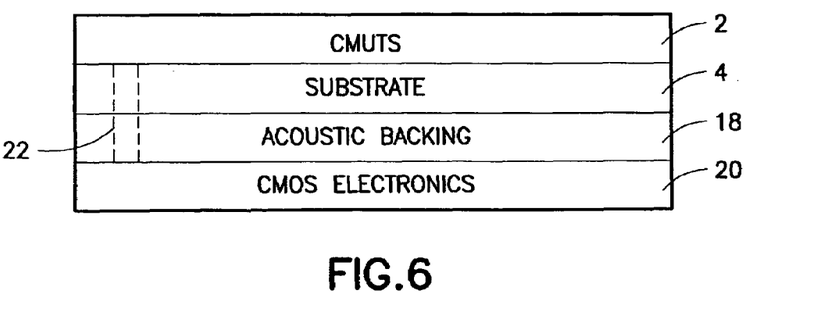
FIG. 6 is a drawing showing the construction of a cMUT patch probe employed in the disclosed embodiment of the invention. In the depicted example, the cMUT cells have been surface micromachined on the substrate. However, the cMUT cells could alternatively be bulk micromachined on the substrate, in which case the solid line at the interface of the cMUT and substrate layers could be changed to a dashed line.

In accordance with one embodiment of the present invention shown in FIG. 6, an array of cMUT subelements is built on one silicon wafer and conventional complementary metal oxide semiconductor (CMOS) switches and preamplifier/buffer circuits are formed on a second silicon wafer to provide a cMUT patch having reconfigurable beamforming elements. An acoustic backing layer 18 is preferably sandwiched between the cMUT wafer 2/4 and the CMOS wafer 20 with vias 22 for passage of electrical connections between the wafers.

The acoustic backing material 18 should have a composition that is acoustically matched to the cMUT substrate 4, to prevent reflection of the acoustic energy back into the device. In the case where the substrate is made of silicon, one example of a suitable backing material comprises a mixture of 96.3% (by mass) tungsten (of which 85% was 10 micron and 15% was 1 micron particle size) and 3.67% polyvinyl chloride (PVC) powders, as disclosed in U.S. Pat. No. 6,831,394 entitled "Backing Material for Micromachined Ultrasonic Transducer Devices". The person skilled in the art will recognize that the composition of the acoustic backing material can be varied from the example given above, However, the acoustic impedance of the resulting backing material should be matched to that of the substrate material. For example, if the substrate is silicon, the acoustic impedance should be approximately 19.8 MRayls±5%.

The CMOS electronics preferably includes the transmit and receive circuits (including a respective transmit/receive switch for each cMUT subelement) and at least a portion of the beamforming circuits. The CMOS electronics also include switches that enable reconfiguration of the subelements, allowing an aperture to be translated over the two-dimensional active area of the transducer. The shape of the apertures is determined by the desired steering angle for the ultrasound beam.

Figure 7:
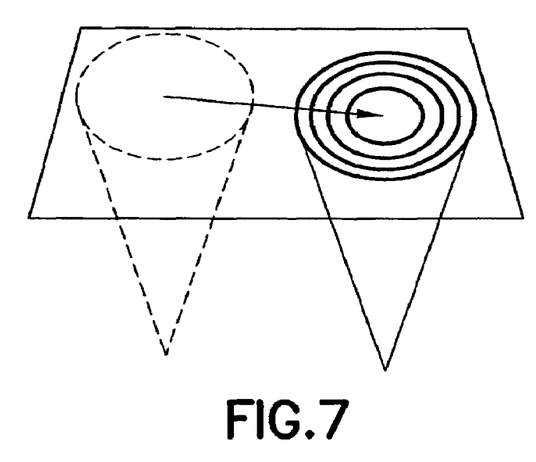
FIG. 7 is a drawing showing scanning of an ultrasound beam, which can be repeated frequently to generate a rectilinear two-dimensional image.
Figure 8:
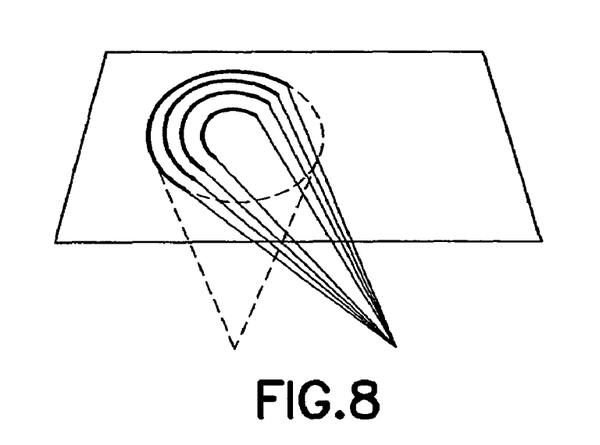
FIG. 8 is a drawing showing steering of an ultrasound beam away from the normal direction.

The beams can be translated across the cMUT patch by translating the annular array of activated subelements (seen in FIG. 5) across the patch as shown in FIG. 7. A uniform translation of the beamforming coefficients produces a new beam at a different location. Repeated frequently, this generates a rectilinear two-dimensional image. An additional bilinear term in the beamforming coefficients produces a beam directed away from the normal, as seen in FIG. 8.

While the invention has been described with reference to preferred embodiments, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. Therefore it is intended that the invention not be limited to the particular embodiment disclosed as the best mode contemplated for carrying out this invention, but that the invention will include all embodiments falling within the scope of the appended claims.

As used in the claims, the term "data processing means" means one or more digital signal processors, one or more microprocessors, one or more computers, one or more computer or processor chips, any combination thereof, and any functionally equivalent circuitry, as well as any associated memory device or memory chip for storing executable instructions or data. As used in the claims, the term "different sample volumes" means sample volumes that either overlap only partially or do not overlap (i.e., occupy the same space) at all.

The invention claimed is:

1. A method for monitoring fetal heart rate, comprising the following steps:
    (a) attaching a first ultrasonic transducer array comprising micromachined ultrasonic transducers to a first area on the exterior of an abdomen of a pregnant woman;
    (b) controlling said first ultrasonic transducer array to transmit beams of pulsed ultrasonic wave energy into the abdomen that are steered at an angle that causes the beams to intersect a fetal heart inside the abdomen;
    (c) acquiring acoustic data by transducing ultrasound wave energy returned from the abdomen of the pregnant woman after each transmission in step (b), the acoustic data being acquired using short range gates; and
    (d) calculating a fetal heart rate based at least in part on the acoustic data acquired in step (c).

2. The method as recited in claim 1, further comprising the following steps performed after step (a) and prior to step (b):
    (e) controlling said first ultrasonic transducer array to scan the abdomen of the pregnant woman by transmitting beams of pulsed ultrasonic wave energy into the abdomen, said beams being steered at different angles;
    (f) acquiring acoustic data by transducing ultrasound wave energy returned from the abdomen of the pregnant woman after each transmission in step (e), the acoustic data being acquired using long range gates, relative to the range gate size in step (c); and
    (g) detecting a pattern in the acoustic data acquired in step (f), said pattern representing a fetal heart signature,
    wherein the beams transmitted in step (b) are steered at an angle equal to or approximately equal to the angle of a beam transmitted in step (e) that resulted in the detection of said pattern in said acquired data in step (g).

3. The method as recited in claim 2, wherein step (g) comprises the step of recognizing an oscillating mean frequency of the Doppler shift in a certain frequency range.

4. The method as recited in claim 1, further comprising the step of adjusting the range gate in step (c) to optimize the signal-to-noise ratio.

5. The method as recited in claim 1, further comprising the following steps performed prior to step (a):
    (e) controlling said first ultrasonic transducer array to transmit a beam of pulsed ultrasonic wave energy;
    (f) acquiring acoustic data by transducing ultrasound wave energy returned from the abdomen of the pregnant woman after each transmission in step (h);
    (g) converting said acquired acoustic data into audible signals; and
    (h) adjusting the position of said first ultrasonic transducer array relative to the abdomen of the patient until the audible signal corresponds to the fetal heart beat, said first ultrasonic transducer array being attached in step (a) at the location where this audible event occurs.

6. The method as recited in claim 1, further comprising the following steps:
    (e) controlling said first ultrasonic transducer array to transmit beams of pulsed ultrasonic wave energy into the abdomen that are steered at respective different angles which are respectively displaced relative to the angle of the beams transmitted in step (b);
    (f) acquiring acoustic data by transducing ultrasound wave energy returned from the abdomen of the pregnant woman after each transmission in step (e);

(g) determining the signal-to-noise ratio of the acquired acoustic data for each different beam steering angle in step (e);
(k) controlling said first ultrasonic transducer array to transmit additional beams of pulsed ultrasonic wave energy into the abdomen that are steered at the beam steering angle which produced a maximum in the signal-to-noise ratio in step (g);
(l) acquiring acoustic data by transducing ultrasound wave energy returned from the abdomen of the pregnant woman after each transmission in step (k); and
(m) calculating a fetal heart rate based on the acoustic data acquired in step (l).

7. The method as recited in claim 6, wherein in step (f) the acoustic data is acquired using different range gates for the same receive beam steering angle.

8. The method as recited in claim 1, further comprising the following steps:
attaching a second ultrasonic transducer array to a second area on the exterior of the abdomen of said pregnant woman; and
performing steps similar to steps (b) through (d), except using said second ultrasonic transducer array instead of said first ultrasonic transducer array.

9. A method for monitoring fetal heart rate, comprising the following steps:
(a) attaching a first ultrasonic transducer array to a first area on the exterior of an abdomen of a pregnant woman;
(b) controlling said first ultrasonic transducer array to scan the abdomen of the pregnant woman by transmitting beams of pulsed ultrasonic wave energy into the abdomen, said beams being steered at different angles;
(c) acquiring acoustic data by transducing ultrasound wave energy returned from the abdomen of the pregnant woman after each transmission in step (b), the acoustic data being acquired using long range gates;
(d) detecting a pattern in the acoustic data acquired in step (c), said pattern representing a fetal heart signature;
(e) controlling said first ultrasonic transducer array to transmit beams of pulsed ultrasonic wave energy into the abdomen that have a short range gate, relative to the range gate size in step (c), and are steered at an angle equal to or approximately equal to the angle of a beam transmitted in step (b) that resulted in the detection of said pattern in said acquired data;
(f) acquiring acoustic data by transducing ultrasound wave energy returned from the abdomen of the pregnant woman after each transmission in step (e); and
(g) calculating a fetal heart rate based at least in part on the acoustic data acquired in step (f).

10. The method as recited in claim 9, wherein step (d) comprises the step of recognizing an oscillating mean frequency of the Doppler shift in a certain frequency range.

11. The method as recited in claim 9, further comprising the step of adjusting the range gate in step (f) to optimize the signal-to-noise ratio.

12. The method as recited in claim 9, wherein said first ultrasonic transducer array comprises micromachined ultrasonic transducers.

13. The method as recited in claim 9, further comprising the following steps performed prior to step (a):
(h) controlling said first ultrasonic transducer array to transmit beams of pulsed ultrasonic wave energy;
(i) acquiring acoustic data by transducing ultrasound wave energy returned from the abdomen of the pregnant woman after each transmission in step (h);
(j) converting said acquired acoustic data into audible signals; and
(k) adjusting the position of said first ultrasonic transducer array relative to the abdomen of the patient until the audible signal corresponds to the fetal heart beat, said first ultrasonic transducer array being attached in step (a) at the location where this audible event occurs.

14. The method as recited in claim 9, further comprising the following steps:
(h) controlling said first ultrasonic transducer array to transmit beams of pulsed ultrasonic wave energy into the abdomen that are steered at respective different angles which are respectively displaced relative to the angle of the beams transmitted in step (e);
(i) acquiring acoustic data by transducing ultrasound wave energy returned from the abdomen of the pregnant woman after each transmission in step (h);
(j) determining the signal-to-noise ratio of the acquired acoustic data for each different beam steering angle in step (h);
(k) controlling said first ultrasonic transducer array to transmit additional beams of pulsed ultrasonic wave energy into the abdomen that are steered at the beam steering angle which produced a maximum in the signal-to-noise ratio in step (j);
(l) acquiring acoustic data by transducing ultrasound wave energy returned from the abdomen of the pregnant woman after each transmission in step (k); and
(m) calculating a fetal heart rate based on the acoustic data acquired in step (l).

15. The method as recited in claim 9, further comprising the following steps:
attaching a second ultrasonic transducer array to a second area on the exterior of the abdomen of said pregnant woman; and
performing steps similar to steps (b) through (g), except using said second ultrasonic transducer array instead of said first ultrasonic transducer array.

16. A method of tracking a moving fetal heart inside an abdomen of a patient, comprising the following steps:
(a) attaching an ultrasonic transducer array comprising micromachined ultrasonic transducers to an area on the exterior of an abdomen of a pregnant woman;
(b) scanning a volume inside the abdomen with beams of pulsed ultrasonic wave energy;
(c) acquiring acoustic data by transducing ultrasound wave energy returned from the abdomen after each transmission in step (b), the acoustic data being acquired using range gates centered in different sample volumes;
(d) determining the signal-to-noise ratio of the acquired acoustic data for each different range gate; and
(e) determining which one of said different range gates had the acoustic data which produced a maximum signal-to-noise ratio.

17. The method as recited in claim 16, further comprising the following steps:
(f) transmitting beams of pulsed ultrasonic wave energy;
(g) acquiring acoustic data by transducing ultrasound wave energy returned from the abdomen after each transmission in step (f), the acoustic data being acquired using the range gate determined in step (e); and
(h) calculating a fetal heart rate based on at least the acoustic data acquired in step (g).

18. The method as recited in claim 17, further comprising the following steps performed after step (h):
(i) scanning a volume inside the abdomen with beams of pulsed ultrasonic wave energy;

(j) acquiring acoustic data by transducing ultrasound wave energy returned from the abdomen after each transmission in step (i), the acoustic data being acquired in range gates centered in different sample volumes adjacent the sample volume in which the range gate determined in step (e) was centered;

(k) determining the signal-to-noise ratio of the acquired acoustic data for each different range gate used in step (i); and (l) determining from which one of said different range gates used in step (i) acoustic data was acquired having a maximum signal-to-noise ratio.

19. A system for autonomous monitoring of heart rate in a fetus, comprising an array of ultrasonic transducer elements, said array comprising a multiplicity of micromachined ultrasonic transducer cells built on or formed in a first substrate, data processing means, and means for delivering signals derived from the output of said array to said data processing means, wherein said data processing means are programmed to perform the following steps:
   (a) controlling said array to transmit beams of pulsed ultrasonic wave energy;
   (b) beamforming acoustic data output from said array in response to impinging ultrasound wave energy transmitted to and returned from the fetal heart; and
   (c) computing the fetal heart rate based on the beamformed acoustic data.

20. The system as recited in claim 19, further comprising CMOS electronics built on or formed in a second substrate, said first and second substrates being bonded together to form a patch suitable for adhesion to a patient.

21. The system as recited in claim 20, wherein said data processing means comprise a digital signal processor, and said signal delivering means comprise a cable.

22. The system as recited in claim 19, wherein said data processing means are further programmed to perform the step of detecting a pattern in the beamformed acoustic data, said pattern representing a fetal heart signature.

23. The system as recited in claim 19, wherein said data processing means are further programmed to perform the step of adjusting the range gate to optimize the signal-to-noise ratio.

24. The system as recited in claim 19, wherein said ultrasonic beams are transmitted in step (a) using a generally circular active aperture.

25. The system as recited in claim 19, wherein step (a) comprises the step of activating concentric, generally annular transducer elements with beamforming delays.

26. A system for autonomous monitoring of heart rate in a fetus, comprising an array of ultrasonic transducer elements, data processing means, and means for delivering signals derived from the output of said array to said data processing means, wherein said data processing means are programmed to perform the following steps:
   (a) controlling said ultrasonic transducer array to scan the abdomen of the pregnant woman by transmitting beams of pulsed ultrasonic wave energy into the abdomen, said beams being steered at different angles;
   (b) acquiring acoustic data by transducing ultrasound wave energy returned from the abdomen of the pregnant woman after each transmission in step (a), the acoustic data being acquired using long range gates;
   (c) detecting a pattern in the acoustic data acquired in step (b), said pattern representing a fetal heart signature;
   (d) controlling said ultrasonic transducer array to transmit beams of pulsed ultrasonic wave energy into the abdomen that are steered at an angle equal to or approximately equal to the angle of a beam transmitted in step (a) that resulted in the detection of said pattern in said acquired data;
   (e) acquiring acoustic data by transducing ultrasound wave energy returned from the abdomen of the pregnant woman after each transmission in step (d), the acoustic data being acquired using short range gates, relative to the range gate size in step (b); and
   (f) calculating a fetal heart rate based at least in part on the acoustic data acquired in step (e).

27. The system as recited in claim 26, wherein step (c) comprises the step of recognizing an oscillating mean frequency of the Doppler shift in a certain frequency range.

28. The system as recited in claim 26, wherein said data processing means are further programmed to perform the step of adjusting the range gate in step (e) to optimize the signal-to-noise ratio.

29. The system as recited in claim 26, wherein said ultrasonic transducer array comprises micromachined ultrasonic transducers.

30. The system as recited in claim 26, wherein said data processing means are further programmed to perform the following steps:
   (g) controlling said first ultrasonic transducer array to transmit beams of pulsed ultrasonic wave energy into the abdomen that are steered at respective different angles which are respectively displaced relative to the angle of the beams transmitted in step (d);
   (h) acquiring acoustic data by transducing ultrasound wave energy returned from the abdomen of the pregnant woman after each transmission in step (g);
   (i) determining the signal-to-noise ratio of the acquired acoustic data for each different beam steering angle in step (g);
   (j) controlling said first ultrasonic transducer array to transmit additional beams of pulsed ultrasonic wave energy into the abdomen that are steered at the beam steering angle which produced a maximum in the signal-to-noise ratio in step (i);
   (k) acquiring acoustic data by transducing ultrasound wave energy returned from the abdomen of the pregnant woman after each transmission in step (j); and
   (l) calculating a fetal heart rate based on the acoustic data acquired in step (k).

31. A system for tracking a fetal heart, comprising an array of ultrasonic transducer elements, data processing means, and means for delivering signals derived from the output of said array to said data processing means, wherein said data processing means are programmed to perform the following steps:
   (a) scanning a volume inside the abdomen with beams of pulsed ultrasonic wave energy;
   (b) acquiring acoustic data by transducing ultrasound wave energy returned from the abdomen after each transmission in step (a), the acoustic data being acquired using range gates centered in different sample volumes;
   (c) determining the signal-to-noise ratio of the acquired acoustic data for each different range gate; and
   (d) determining which one of said different range gates had the acoustic data which produced a maximum signal-to-noise ratio.

32. The system as recited in claim 31, further comprising the following steps:
   (e) transmitting beams of pulsed ultrasonic wave energy;
   (f) acquiring acoustic data by transducing ultrasound wave energy returned from the abdomen after each transmission in step (e), the acoustic data being acquired using the range gate determined in step (d); and (g) calculating a fetal heart rate based on at least the acoustic data acquired in step (f).

33. The system as recited in claim 32, further comprising the following steps performed after step (g):

(h) scanning a volume inside the abdomen with beams of pulsed ultrasonic wave energy;

(i) acquiring acoustic data by transducing ultrasound wave energy returned from the abdomen after each transmission in step (h), the acoustic data being acquired in range gates centered in different sample volumes adjacent the sample volume in which the range gate determined in step (d) was centered;

(j) determining the signal-to-noise ratio of the acquired acoustic data for each different range gate used in step (i); and (k) determining from which one of said different range gates used in step (i) acoustic data was acquired having a maximum signal-to-noise ratio.

* * * * *